United States Patent [19]
Painter et al.

[11] Patent Number: 6,117,435
[45] Date of Patent: Sep. 12, 2000

[54] NATURAL LOOK COSMETIC COMPOSITIONS

[75] Inventors: Rachel J. Painter, E. Setauket; Isaac D. Cohen, Brooklyn, both of N.Y.

[73] Assignee: Color Access, Inc., Melville, N.Y.

[21] Appl. No.: 09/103,989

[22] Filed: Jun. 24, 1998

[51] Int. Cl.⁷ .............................. A61K 7/021; A61K 9/14; A61K 31/74
[52] U.S. Cl. .............................. 424/401; 63/69; 63/78.02; 63/489; 63/401; 514/828
[58] Field of Search ................................. 424/78.03, 401, 424/63, 69; 514/828

[56] References Cited

U.S. PATENT DOCUMENTS

| | | | |
|---|---|---|---|
| 5,082,660 | 1/1992 | Ounanian et al. | 424/63 |
| 5,800,816 | 9/1998 | Brieva et al. | 424/63 |
| 5,853,712 | 12/1998 | Langlois | 424/78.03 |
| 5,888,879 | 3/1999 | Nishikata et al. | 424/401 |
| 5,919,467 | 7/1999 | Jenkins et al. | 424/401 |

FOREIGN PATENT DOCUMENTS

| | | |
|---|---|---|
| 6-056628 | 3/1994 | Japan . |
| WO 9811865 | 3/1998 | WIPO . |

OTHER PUBLICATIONS

K. Nishikata, "A Natural Looking Make–up," Cosmetic & Toiletries, vol. 112, May 1997 (1997–05), pp. 9–55.

Primary Examiner—Thurman K. Page
Assistant Examiner—S. Howard
Attorney, Agent, or Firm—Kenyon & Kenyon

[57] ABSTRACT

The invention relates to a composition for topical application to the skin comprising (a) silica beads comprising an inner core of silica, a middle layer of metal oxide, and an outer layer of silica; (b) at least one interference pigment; and optionally (c) at least one non-interference pigment, in a cosmetically or pharmaceutically acceptable vehicle. The compositions of the invention confer a natural appearance to the skin, also reducing the appearance of flaws or defects in the skin without conferring an opaque or made-up appearance.

36 Claims, No Drawings

NATURAL LOOK COSMETIC COMPOSITIONS

FIELD OF THE INVENTION

The present invention relates to cosmetic compositions. More specifically, the invention relates to cosmetic compositions which have a natural appearance on the skin.

BACKGROUND OF THE INVENTION

The appearance of what we typically think of as attractive, natural-looking skin is influenced by a number of factors. It is generally accepted that a "standard" beautiful skin has a transparent quality about it, with uniform undertones of color. The basis for what we regard as this natural appearance lies in the skin structure itself. The outer layer of human skin is a semi-transparent layer known as the stratum corneum. The transparency of the stratum corneum permits glimpses of the deeper layers of skin, where blood vessels and pigments reside; the reddish hue of the blood vessels' hemoglobin, with the brown/black hue of melanin, the primary skin pigment, combine to produce what we view as the skin's color. Of course, in addition to ideal skin having the transparent look with a uniform color distribution, it should also be smooth and even, with no apparent surface flaws. Needless to say, few individuals can ever hope to meet such a standard without some outside assistance. Thus, a wide variety of cosmetics exist to help out where nature has failed.

In ancient times, although makeup was worn on facial skin, it was seldom intended to mimic the actual appearance of natural, but perfect, skin; in many cases, it was frankly and intentionally artificial-looking. In recent times, however, the trend has been toward more natural-looking makeups. In particular, one of the long-sought goals has been the development of a foundation that does not give the user a "made-up" look. In reality, however, it is difficult to accomplish the goal of achieving coverage of flaws and unevenness of skin tone, while still maintaining the vibrant look of clean bare skin. This is primarily because those components of makeups which provide the desired color and coverage, such as the titanium or iron oxide pigments, are largely opaque, and therefore obscure that sought-after vibrant transparency. Although in recent years, transparent pigments have become available, the coverage needed to mask flaws in the surface of the skin is frequently lacking.

Clearly, there are competing goals in the development of a natural-looking makeup which, given currently available technology, seem difficult, if not impossible to resolve. Very recently, the cosmetics industry has turned to a detailed study of the optics of light absorption, reflection and scattering in the skin in an attempt to design a product which, when applied to the skin, will convey to the viewer the impression of a natural but flawless clean skin (See, for example, Nishikata et al., Cosmetics and Toiletries 112: 39–55, 1997). It has, for example, been recognized that the angle of viewing of the skin will alter the appearance to the viewer: the viewer will see more of the red of hemoglobin in the skin's dermis when the skin is viewed at close to a perpendicular angle, while brown, due to the melanin content of the outer layers of epidermis, will predominate when the skin is viewed at a shallower angle. Although strides have been made in the understanding of the optical events leading to our perception of natural-looking skin, the development of products based on this knowledge has not to date been fully realized. However, the present invention represents a substantial advance in the preparation of a cosmetic which conveys the transparency and color of natural skin, while providing considerable masking of surface flaws.

SUMMARY OF THE INVENTION

The present invention relates to a composition for topical application to the skin which mimics the natural appearance of bare skin, yet provides sufficient coverage and/or light diffusion to hide surface flaws in the skin. The composition comprises three components: (a) silica beads comprising a silica core, coated with a thin inner layer of ultrafine metal oxide, and an outer layer of silica; (b) at least one interference pigment; and, optionally, (c) at least one non-interference pigment, in combination with a cosmetically acceptable vehicle. The compositions can be color cosmetic compositions, such as foundations, powders, eyeshadows, blushes, lip products, and the like, as well as treatment products which, when applied, although not intended to color, impart a natural appearance to the skin, whether used alone in combination with makeup.

DETAILED DESCRIPTION OF THE INVENTION

The compositions of the invention successfully simulate the look of bare skin by incorporating components each of which effectively mimics one of the actual components which contribute to the skin's natural appearance, i.e., stratum corneum, hemoglobin, and melanin. The stratum corneum component of the composition is represented by silica beads. The beads employed may have a diameter of from about 0.5 to about $20\mu$, more preferably from about 1 to about $10\mu$, and most preferably about 4 to about $8\mu$. A larger particle size is preferred as the smaller particle sizes tend to be more opaque. The silica bead comprises a core of silica, representing from about 50–90%, preferably about 70–90% by weight of the total bead; a middle layer of ultrafine metal oxide, comprising from about 1–10%, preferably about 1–5% by weight of the total bead; and an outer layer of silica, comprising from about 1–20%, preferably about 5–15% by weight of the total bead. In a preferred embodiment, the metal oxide is titanium dioxide, but can also be zinc or iron oxide. The particle as a whole may be coated or uncoated, depending upon the nature of the vehicle in which it will be used. For example, when employed in a water-in-oil formulation, a hydrophobic coating on the particle is preferred. Examples of suitable hydrophobic coatings include, but are not limited to, silicones, such as methicone, dimethicone, silanes, polyethylene, metal soaps, lecithin, waxes, nylon or fluorochemicals. A particularly suitable silica bead is commercially available from US Cosmetics under the name SINP-OSD-SW-6(LHC). This bead is approximately $6\mu$ in diameter, comprising a silica core(about 85%), a thin layer of ultrafine titanium dioxide layer (about 5%), and an outer layer of silica (about 10%), treated with a coating of low hydrogen methicone. As a guideline, the amount of silica beads used in the composition is generally in the range of from about 1 to about 90%, preferably about 1–50%, more preferably about 5–30%, by weight of the total composition; however, it should be understood that the amount used will vary depending on the type of product being made, liquids generally using lower levels, and powders and hot pours typically using higher levels.

The hemoglobin component is represented in the composition by at least one interference pigment. Interference pigments, for purposes of the present specification and claims, are defined as thin platelike layered particles having a high refractive index, which, at a certain thickness, produce interference colors, resulting from the interference of typically two, but occasionally more, light reflections, from different layers of the plate. The most common examples of interference pigments are micas layered with 50–300 nm films of $TiO_2$, $Fe_2O_3$, or $Cr_2O_3$. Such pigments are often pearlescent, and may be uncoated or coated. Coatings include, but are not limited to, silica, nylon or polymethylmethacrylate(PMMA). Useful interference pigments are available commercially from a wide variety of suppliers, for example, Rona (Timiron™ and Dichrona™), Presperse(Flonac™), Englehard(Duochrome™), and Kobo (SK-45-R and SK-45-G). Examples of particularly useful products are a mica coated with a thin layer of $TiO_2$ and further coated with beads of PMMA (Kobo-LSBPA050/MicaR), which yields an attractive red color without the undesirable pearliness; and Flamenco Red(Engelhard), a $TiO_2$ coated mica. It may often be desirable to combine interference pigments of different colors or types so as to blend an appropriate shade or intensity of color. The size of the interference pigment can be varied, depending upon the effect desired. Generally, a smaller pigment is less pearly, and therefore preferred, as the larger pigments will confer a substantial amount of sparkle. A useful size range of the interference particles is from about 1 to about $200\mu$, and preferably is about 3 to about $100\mu$. The interference pigment is used in an amount of from about 0.05%–90% by weight, with the high end of the range being most appropriate for use in a pressed powder product. However, in most types of products, the amounts of interference pigment will range from about 0.5% to about 15%, the lower end of the range being used in unpigmented(i.e., having no non-interference pigments) or lightly pigmented products, and the higher end of this range being used in more heavily pigmented products. Given this guidance, it is within the skill of the art to determine an optimum concentration of interference pigment to achieve the final look desired. Also, as with the silica beads, when the vehicle is a water-in-oil or water-in-silicone emulsion, it may be desirable to coat the interference pigments with a hydrophobic coating, to facilitate wetting out.

The combination of the silica bead and interference pigment, when applied to the skin, provides a very natural looking appearance or a "glow" to the skin. However, for a foundation, or other makeup product, it is often desirable to add a color component to match the color of the wearer's skin, i.e., to mimic the skin's melanin component. This is provided by the presence of at least one non-interference pigment. Examples of useful inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white), zinc oxide and mixtures thereof. Also useful are transparent metal oxide-coated silica beads. Metal oxides, particularly iron and titanium oxides, are preferred non-interference pigments in the composition of the invention, particularly for foundations.

Organic pigments, however, can also be used in the compositions of the invention; these include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Stains, such as bromo dyes and fluorescein dyes can also be employed. The amount and type of pigment used will vary depending upon the nature of the final product and the desired intensity of color; generally, however, the amount of non-interference pigment will be about 1 to about 20% by weight of the total composition. It will be apparent to those skilled in the art that those compositions intended to confer a greater level of coverage to the skin will contain more pigment than those intended to enhance but not necessarily cover the skin. In addition, microfine particulate pigments can be used at somewhat higher levels than those of normal particle size without significantly increasing the level of opacity of the composition on the skin.

An optional component of the formulation are spherical powders which can aid in reducing or softening any metallic look that may result from one of the other components, particulaly the interference pigment. Such materials are known in the cosmetic industry for their light-scattering properties on the skin. Powders of this type may include, but are not limited to, powders comprising(with examples of commercially available sources) calcium aluminum borosilicate (Luxsil™), PMMA (Microsphere M-100), polyethylene (polyethylene Cl 2080), methyl methacrylate crosspolymer (Covabeads LH85), nylon-12 (Orgasol 2002 O Nat Cos C), or ethylene/acrylic acid copolymer (Flobeads EA209). These powders, when used, are present in an amount of from about 0.001% to about 20%, preferably about 1% to about 10%, by weight of the total composition.

The combined components can be used in any type of skin treatment or makeup product. Skin treatment products, such as lip products, acne treatments, moisturizers, anti-aging products, lifting treatments, cellulite treatments and eye treatments, will ordinarily contain only the multilayered silica beads and the interference pigments; however, makeup products will typically contain all three components. The makeup products of the invention include, but are not limited to, foundations, blushes, pressed or loose powders, concealers, bronzers, eyeshadows, eyeliners, lipsticks, and lipglosses. The products of the invention can take any form which is typical of cosmetic products, for example, hot pour formulations, water-in-oil emulsions, oil-in-water emulsions, gels, sticks, sprays, anhydrous formulations, and pressed or loose powders. There is no limitation on the type of vehicle that can be employed. In particular, the preferred identity of the vehicle will be largely controlled by the type of product into which the components are to be incorporated. For a liquid foundation, for example, a water-in-oil emulsion is preferred for aesthetic reasons, and although the oil portion of the vehicle can be any which is typically used for this purpose, it is preferred that the oil component comprise a silicone oil, either volatile or non-volatile. On the other hand, in a hot-pour formulation, the components are preferably dispersed in a hydrocarbon vehicle, such as isododecane or polyisobutene. In a preferred embodiment, the effect of the combined components are seen to best advantage in a hot pour product, such as a solid foundation or cheek color. In both cases, however, it is preferred that each of the pigments be hydrophobically coated, so as to facilitate formulation.

The formulation also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as octyl methoxycinnamate);

particulate sunscreens (such as zinc oxide); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents, such as cholesterol; cationic polymers (such as Polyquaternium 10); anionic polymers (such as xanthan gum); pigment wetting agents, such as Arlacel™ P100, or Emerest™ 2452; vitamins (such as tocopherol); and the like.

The compositions can also encompass one or more active components, and as such can be either cosmetic or pharmaceutical compositions. Examples of useful actives include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, anti-asthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active agents include retinoids such as retinol, and esters, acids, and aldehydes thereof; ascorbic acid, and esters and metal salts thereof; tocopherol and esters and amide derivatives thereof; shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, and mixtures thereof.

Compositions of the invention provide a very natural and attractive appearance on the skin to which they are applied. Since the components have been chosen to mimic the naturally occurring components of the skin, the composition in place on the skin undergoes the same angle-dependent color changes as natural skin, i.e., red is perceived when viewed perpendicularly and brown when viewed at a shallower angle; these effects are not only visually detectable, but also quantifiable. In addition, the compositions, by virtue of the way in which light interacts with the components of the composition on the skin, permit a reduction in the appearance of skin flaws and defects; this reduces or eliminates the necessity for building any significant level of coverage into the formulation, thereby also reducing or eliminating the "made-up" look which results from the use of such formulations, particularly on older users.

The invention is further illustrated by the following non-limiting examples.

EXAMPLES

Example 1

This example illustrates the preparation of a hot-pour formulation of the invention:

| Component | Weight % |
| --- | --- |
| Phase I | |
| isotetracosane | 25.30 |
| isoeicosane | 5.50 |
| polyglyceryl-3-diisostearate | 1.00 |
| carnauba wax | 3.00 |
| isododecane/Quaternium-18 hectorite/ triethylcitrate | 6.00 |
| Phase II | |
| multilayered silica beads | 14.00 |
| nylon-12 | 5.50 |
| HDI/trimethylol hexyllactone crosspolymer | 9.50 |
| TiO$_2$/methicone-coated mica | 10.00 |
| propyl paraben | 0.20 |
| Phase III | |
| isotetracosane | 10.00 |
| silane-coated iron oxides | 2.30 |
| methicone-coated TiO$_2$ | 7.70 |

Phase I ingredients are combined together at 90° C. The components are mixed until the wax and hectorite are thoroughly dispersed. Phase II ingredients are added to Phase I ingredients at 90° C., and mixed until smooth. The Phase III materials are combined, and ground in a roller mill three times. The pigment grind is then added to phases I and II at 90° C., and mixed until homogeneous. The mixture is then poured into pans at 90° C. and allowed to cool to room temperature.

Example II

This example illustrates the preparation of a water-in-silicone emulsion of the invention.

| Component | Weight % |
| --- | --- |
| Phase I | |
| phenyl trimethicone | 10.50 |
| phenyltrimethicone/Quaternium-18 hectorite/ triethylcitrate | 2.00 |
| BHT | 0.10 |
| propyl paraben | 0.10 |
| iron oxides | 1.20 |
| methicone-coated TiO$_2$ | 3.80 |
| Phase II | |
| cyclomethicone | 10.00 |
| cyclomethicone/dimethicone copolyol | 16.00 |
| laureth-7 | 0.50 |
| Phase III | |
| multilayered silica beads | 7.00 |
| TiO$_2$-coated mica | 10.00 |
| Phase IV | |
| purified water | 36.30 |
| phenoxyethanol | .50 |
| magnesium sulfate | 2.00 |

Phase I components are mixed together and passed through a roller mill three times. Phase II components are mixed together in a primary vessel. The Phase I grind is added to Phase II and mixed to homogeneity. Phase III ingredients are added into Phases I and II, and mixed to homogeneity. Phase IV components are mixed at 35° C. until clear, and cooled to room temperature. Ten percent of the Phase IV mixture is seeded into Phases I–III, and mixed for five minutes, then the remainder of Phase IV is added. The entire batch is then homogenized for 15 minutes.

What we claim is:

1. A composition for topical application to the skin comprising (a) silica beads comprising an inner core of silica, a middle layer of metal oxide, and an outer layer of silica; (b) at least one interference pigment; and optionally (c) at least one non-interference pigment, in cosmetically or pharmaceutically acceptable vehicle.

2. The composition of claim 1 in which the silica beads have an average diameter of between about 0.5 to about 20 microns.

3. The composition of claim 1 in which the interference pigment is mica.

4. The composition of claim 1 in which the silica beads have an average diameter of about 1 to about 10 microns.

5. The composition of claim 1, in which the silica beads have an average diameter of about 4 to about 8 microns.

6. The composition of claim 3 in which the mica is coated with titanium dioxide.

7. The composition of claim 1 in which the non-interference pigment comprises at least one inorganic pigment.

8. The composition of claim 7 in which the inorganic pigment is selected from the group consisting of iron oxide, ferric ammonium ferrocyanide, manganese violet, ultramarine blue, chrome oxide, talc, lecithin modified talc, zeolite, kaolin, lecithin modified kaolin, titanium dioxide, zinc oxide, metal oxide-coated silica beads, and mixtures thereof.

9. The composition of claim 7 in which the non-interference pigment comprises a metal oxide.

10. The composition of claim 1 in which the non-interference pigment comprises at least one organic pigment.

11. The composition of claim 10 in which the organic pigment is selected from the group consisting of phthalocyanine blue and green pigment, diarylide yellow and orange pigments, azo red and yellow pigments, lakes, fluorescein dyes, and bromo dyes.

12. The composition of claim 1 which does not contain a non-interference pigment.

13. The composition of claim 12 which is a skin-care product.

14. The composition of claim 13 which is a moisturizer.

15. The composition of claim 1 which also comprises a light-scattering spherical powder.

16. A composition for topical application to the skin comprising (a) silica beads comprising an inner core of silica, a middle layer of metal oxide, and an outer layer of silica, the beads having an average diameter of between about 1 to 10 microns; (b) a mica interference pigment; and (c) a non-interference pigment; in a cosmetically or pharmaceutically acceptable vehicle.

17. The composition of claim 16 in which the silica beads have an average diameter of about 6 microns; the interference pigment is a mica coated with a metal oxide; and the non-interference pigment is a metal oxide.

18. The composition of claim 17 in which the silica beads are present in an amount of from about 1 to about 90%, the interference pigment is present in an amount from about 0.05 to about 90%, and the non-interference pigment is present in an amount of from about 1 to about 20%, all by weight of the total composition.

19. The composition of claim 18 in which the silica beads are present in an amount of from about 1 to about 50%, the interference pigment is present in an amount of from about 0.5 to about 15%, and the non-interference pigment is present in an amount of from about 1 to about 12%.

20. The composition of claim 16 which also comprises a light-scattering spherical powder.

21. The composition of claim 20 in which the powder is present in an amount of from about 1% to about 20%.

22. The composition of claim 16 which is a hot pour product.

23. The composition of claim 22 comprising a hydrocarbon oil vehicle.

24. The composition of claim 23 in which the hydrocarbon oil is isododecane or polyisobutene.

25. The composition of claim 24 in which one or more of the pigments is hydrophobically coated.

26. The composition of claim 16 which is a water-in-oil emulsion.

27. The composition of claim 26 in which the oil is a silicone oil.

28. The composition of claim 26 in which one or more of the pigments is hydrophobically coated.

29. A method for imparting a natural look to the skin which comprises applying to the skin a composition according to claim 1.

30. A method for imparting a natural look to the skin which comprises applying to the skin a composition according to claim 13.

31. A method for imparting a natural look to the skin which comprises applying to the skin a composition according to claim 16.

32. A method for imparting a natural look to the skin which comprises applying to the skin a composition according to claim 22.

33. A method for imparting a natural look to the skin which comprises applying to the skin a composition according to claim 26.

34. A method for reducing the appearance of flaws in the skin which comprises applying to the skin a composition according to claim 1.

35. A method for reducing the appearance of flaws in the skin which comprises applying to the skin a composition according to claim 13.

36. A method for reducing the appearance of flaws in the skin which comprises applying to the skin a composition according to claim 16.

* * * * *